(12) United States Patent
Nakazawa

(10) Patent No.: US 10,697,029 B2
(45) Date of Patent: Jun. 30, 2020

(54) SACCHARIFIED SOLUTION PRODUCTION METHOD USING POROUS MEMBRANE

(71) Applicant: ASAHI KASEI KABUSHIKI KAISHA, Tokyo (JP)

(72) Inventor: Yukio Nakazawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 56 days.

(21) Appl. No.: 16/121,939

(22) Filed: Sep. 5, 2018

(65) Prior Publication Data
US 2019/0071740 A1   Mar. 7, 2019

(30) Foreign Application Priority Data

Sep. 7, 2017  (JP) ................................. 2017-171993

(51) Int. Cl.
| | | |
|---|---|---|
| *C13K 1/06* | (2006.01) | |
| *C12P 19/02* | (2006.01) | |
| *C08B 30/12* | (2006.01) | |
| *B01D 71/32* | (2006.01) | |
| *C12P 19/04* | (2006.01) | |
| *B01D 69/02* | (2006.01) | |
| *B01D 69/08* | (2006.01) | |
| *C12P 19/14* | (2006.01) | |
| *B01D 65/02* | (2006.01) | |

(52) U.S. Cl.
CPC ................ *C13K 1/06* (2013.01); *B01D 69/02* (2013.01); *B01D 69/08* (2013.01); *B01D 71/32* (2013.01); *C08B 30/12* (2013.01); *C12P 19/02* (2013.01); *C12P 19/04* (2013.01); *C12P 19/14* (2013.01); *B01D 65/02* (2013.01); *B01D 2321/168* (2013.01); *B01D 2325/30* (2013.01)

(58) Field of Classification Search
None
See application file for complete search history.

(56) References Cited

U.S. PATENT DOCUMENTS 10,159,938 B2 * 12/2018 Nakamoto ........... B01D 63/024

FOREIGN PATENT DOCUMENTS

JP    2011168741 A    1/2011

* cited by examiner

*Primary Examiner* — Chester T Barry
(74) *Attorney, Agent, or Firm* — Greenblum & Bernstein, P.L.C.

(57) ABSTRACT

A method ensuring excellent chemical resistance to a chemical cleaning solution, excellent filtration performance and an enhanced life in a saccharified solution production method including a cleaning step and filtration using a porous filtration membrane. A method for producing a saccharified solution, including the following steps: a liquefaction step of adding an enzyme to liquid starch to obtain a sugar-containing liquefied product; a saccharification step of adding a saccharifying enzyme to further degrade the sugar and obtain a saccharified solution composition containing a saccharified solution and an insoluble component; a filtration step of passing the saccharified solution composition through a porous membrane composed of a resin having a three-dimensional network structure to separate the saccharified solution from the insoluble component; and a cleaning step of passing or soaking the porous membrane into a cleaning solution to clean/remove the insoluble matter attached to the surface or inside of the porous membrane.

15 Claims, 5 Drawing Sheets

SACCHARIFIED SOLUTION PRODUCTION METHOD USING POROUS MEMBRANE

FIELD

The present invention relates to a saccharified solution production method using a porous membrane and including a cleaning step. More specifically, the present invention relates to a method ensuring excellent resistance to a cleaning solution (chemical solution) in a saccharified solution production method using a porous membrane and including a cleaning step.

BACKGROUND

For example, in a tap water treatment for obtaining drinking water or industrial water from natural water sources such as seawater, river water, lake and marsh water and underground water, which are suspended water, a sewage treatment for treating domestic drainage such as sewage water to produce recycled water and obtain dischargeable clarified water, or a step of removing insoluble components from a saccharified solution in the production of a saccharified solution, a solid-liquid separation operation (clarification operation) is required so as to separate and remove suspended matter. By such a clarification operation, with respect to the tap water treatment, suspended matter (e.g., clay, colloid, bacteria) derived from natural water sources as suspended water are removed; with respect to the sewage treatment, suspended matter (e.g., sludge) in treated water after biological treatment (secondary treatment) with suspended matter, activated sludge, etc. in sewage water are removed; and with respect to the production of a saccharide solution from liquid starch, insoluble components having not been degraded by an enzyme are removed. For the clarification operation of a saccharified solution, a diatomaceous earth filtration method has been heretofore performed, but in recent years, a membrane filtration method is spreading in place of such a method.

Conventionally, these clarification operations have been performed mainly by a pressure flotation method, a precipitation method, a sand filtration method, a coagulation, sedimentation and sand filtration method, a diatomaceous earth filtration method, etc., but recently, a membrane filtration method is spreading instead of these methods. The advantage of the membrane filtration method includes, for example, (1) the clarification level of the obtained water quality is high and stable (safety of the obtained water is high); (2) the installation space of a filtration apparatus can be small; and (3) an automatic operation is easy. For example, in a pretreatment of seawater desalination reverse osmosis filtration, a membrane filtration method is used as a substitute for or a latter step of the pressure flotation method so as to further improve the water quality of treated water subjected to pressure flotation treatment. In the clarification operation by such membrane filtration, a flat membrane or a hollow-fiber porous ultrafiltration or microfiltration membrane, having an average pore size of several nm to several hundred nm, is used.

In this way, the clarification operation by the membrane filtration method has many advantages that the above-described conventional pressure flotation method, sand filtration method, etc. do not have, and its spread to seawater desalination pretreatment, etc. is being encouraged as a substitute for or a complementary means to the conventional methods. In addition, an organic membrane composed of a resin described in Patent Literature 1 below is often used as the porous membrane.

CITATION LIST

Patent Literature

[PTL 1] Kokai (Unexamined Japanese Patent Publication) No. 2011-168741

SUMMARY

Technical Problem

As described above, an organic membrane composed of a resin is often used as a porous membrane, but at the time of manufacture of a porous filtration membrane from a resin material, if the membrane formation method differs, a difference emerges in the microstructure of the material constituting the membrane. Usually, when a filtration operation is continued, the membrane is clogged and therefore, the operation of a filtration method using a porous filtration membrane involves a cleaning step. On the other hand, when a chemical is used in the cleaning step, strength deterioration of the membrane is induced. At this time, if there is a difference in the microstructure of the material constituting the porous filtration membrane, the degree of damage to the porous filtration membrane by a cleaning solution (chemical solution) used in the repeated cleaning step differs, giving rise to a problem that the filtration performance and life are affected.

In consideration of such a problem, the problem to be solved by the present invention is to provide a method ensuring excellent chemical resistance and filtration performance and an enhanced life in a saccharified solution production method using a porous filtration membrane and including a cleaning step using a cleaning solution (chemical solution).

Solution to Problem

As a result of intensive studies and many experiments to solve the problem above, the present inventors have unexpectedly found that when a membrane having good pore continuity from the outer side of membrane, which is a to-be-treated liquid side of a porous filtration membrane, to the inner side of membrane, which is a filtrate side, is used, even if an aqueous solution containing from 0.1 to 4 wt % of sodium hydroxide and/or from 0.01 to 0.5 wt % of sodium hypochlorite is employed as a cleaning solution (chemical solution) used in the cleaning step, the deterioration of the membrane can be kept to a minimum. The present invention has been accomplished based on this finding.

That is, the present invention is as follows.

[1] A method for producing a saccharified solution, including the following steps:

a liquefaction step of adding an enzyme to liquid starch to partially degrade the starch and obtain a sugar-containing liquefied product;

a saccharification step of adding a saccharifying enzyme to the obtained sugar-containing liquefied product to further degrade the sugar and obtain a saccharified solution composition containing a saccharified solution and an insoluble component;

a filtration step of passing the saccharified solution composition through a porous membrane composed of a resin having a three-dimensional network structure to separate the saccharified solution from the insoluble component; and a cleaning step of passing or soaking the porous membrane into a cleaning solution to clean/remove an insoluble matter attached to the surface or inside of the porous membrane; wherein on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 1 μm$^2$ or less is 70% or more relative to the total area of resin parts, and the cleaning solution is an aqueous solution containing from 0.1 to 4 wt % of sodium hydroxide and from 0.01 to 0.5 wt % of sodium hypochlorite.

[2] A method for producing a saccharified solution, including the following steps:

a liquefaction step of adding an enzyme to liquid starch to partially degrade the starch and obtain a sugar-containing liquefied product;

a saccharification step of adding a saccharifying enzyme to the obtained sugar-containing liquefied product to further degrade the sugar and obtain a saccharified solution composition containing a saccharified solution and an insoluble component;

a filtration step of passing the saccharified solution composition through a porous membrane composed of a resin having a three-dimensional network structure to separate the saccharified solution from the insoluble component; and a cleaning step of passing or soaking the porous membrane into a cleaning solution to clean/remove an insoluble matter attached to the surface or inside of the porous membrane; wherein on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 10 μm$^2$ or more is 15% or less relative to the total area of resin parts, and the cleaning solution is an aqueous solution containing from 0.1 to 4 wt % of sodium hydroxide and from 0.01 to 0.5 wt % of sodium hypochlorite.

[3] A method for producing a saccharified solution, including the following steps:

a liquefaction step of adding an enzyme to liquid starch to partially degrade the starch and obtain a sugar-containing liquefied product;

a saccharification step of adding a saccharifying enzyme to the obtained sugar-containing liquefied product to further degrade the sugar and obtain a saccharified solution composition containing a saccharified solution and an insoluble component;

a filtration step of passing the saccharified solution composition through a porous membrane composed of a resin having a three-dimensional network structure to separate the saccharified solution from the insoluble component; and a cleaning step of passing or soaking the porous membrane into a cleaning solution to clean/remove an insoluble matter attached to the surface or inside of the porous membrane; wherein on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 1 μm$^2$ or less is 70% or more relative to the total area of resin parts, and the total of areas of resin parts having an area of 10 μm$^2$ or more is 15% or less relative to the total area of resin parts, and the cleaning solution is an aqueous solution containing from 0.1 to 4 wt % of sodium hydroxide and from 0.01 to 0.5 wt % of sodium hypochlorite.

[4] The method according to any one of [1] to [3] above, wherein with respect to the porous membrane, on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of more than 1 μm$^2$ and less than 10 μm$^2$ is 15% or less relative to the total area of resin parts.

[5] The method according to any one of [1] to [4] above, wherein the surface opening ratio of the porous membrane is from 25 to 60%.

[6] The method according to any one of [1] to [5] above, wherein the relationship between the tensile elongation at break E0 of the porous membrane before the cleaning step and the tensile elongation at break E1 of the porous membrane after the cleaning step is E1/E0×100≥98%.

[7] The method according to any one of [1] to [5] above, wherein the relationship between the tensile elongation at break E0 of the porous membrane before the cleaning step and the tensile elongation at break EX of the porous membrane after repeating the cleaning step X times (X is an integer of 2 to 10) is EX/E0×100≥97%.

[8] The method according to any one of [1] to [7] above, wherein the relationship between the flux L0 of the porous membrane before the filtration step and the flux L1 of the porous membrane after the cleaning step is L1/L0×100≥90%.

[9] The filtration method according to any one of [1] to [7] above, wherein the relationship between the flux L0 of the porous membrane before the filtration step and the flux LX of the porous membrane after repeating the cleaning step X times (X is an integer of 2 to 10) is LX/L0×100≥90%.

[10] The method according to any one of [1] to [9] above, wherein the porous membrane is a hollow-fiber membrane.

[11] The method according to any one of [1] to [10] above, wherein the resin constituting the porous membrane is a thermoplastic resin.

[12] The method according to [11] above, wherein the thermoplastic resin is a fluororesin.

[13] The method according to [12] above, wherein the fluororesin is selected from the group consisting of a vinylidene fluoride resin (PVDF), a chlorotrifluoroethylene resin, a tetrafluoroethylene resin, an ethylene-tetrafluoroethylene copolymer (ETFE), an ethylene-monochlorotrifluoroethylene copolymer (ECTFE), a hexafluoropropylene resin, and a mixture of these resins.

[14] The method according to any one of [1] to [13] above, wherein the cleaning step includes a cleaning solution step of performing cleaning with the cleaning solution and a rinsing step of performing rinsing with rinse water for removing the remaining cleaning solution component.

[15] The method according to [14] above, wherein the amount of rinse water used in the rinsing step is 100 L/m$^2$ or less per unit area of the porous membrane.

[16] The method according to [14] or [15] above, wherein the chlorine concentration in the filtrate at the completion of the rinsing step is 0.1 ppm or less and the pH of the filtered liquid is 8.6 or less.

Advantageous Effects of Invention

In the production method for a saccharified solution according to the present invention, the filtration step uses a membrane having good pore continuity from the inner side of membrane, which is a to-be-treated liquid side of a porous filtration membrane, to the outer side of membrane, which is a filtrate side, so that in the case of using an aqueous solution containing from 0.1 to 4 wt % of sodium hydroxide and/or from 0.01 to 0.5 wt % of sodium hypochlorite for a cleaning solution (chemical solution) used in the cleaning step, the deterioration of the membrane can be kept to a minimum, and therefore, this is a production method ensuring excellent chemical resistance and filtration performance and an enhanced life in a saccharified solution production method using a porous filtration membrane and including a cleaning step using such a chemical solution.

DESCRIPTION OF EMBODIMENTS

Figure 1:
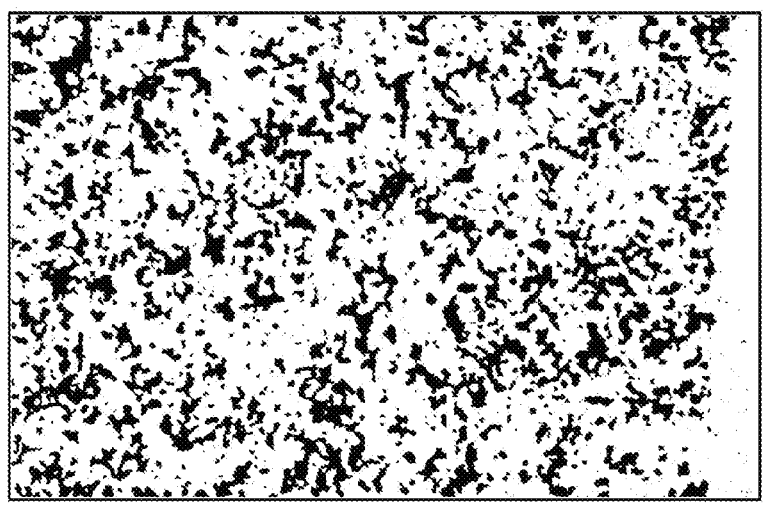
FIG. 1 is one example of an SEM image of a cross-section of a porous membrane used in the saccharified solution composition filtering step of the present embodiment (the black portion and the white portion indicate a resin and a pore (open pore), respectively).
Figure 2:
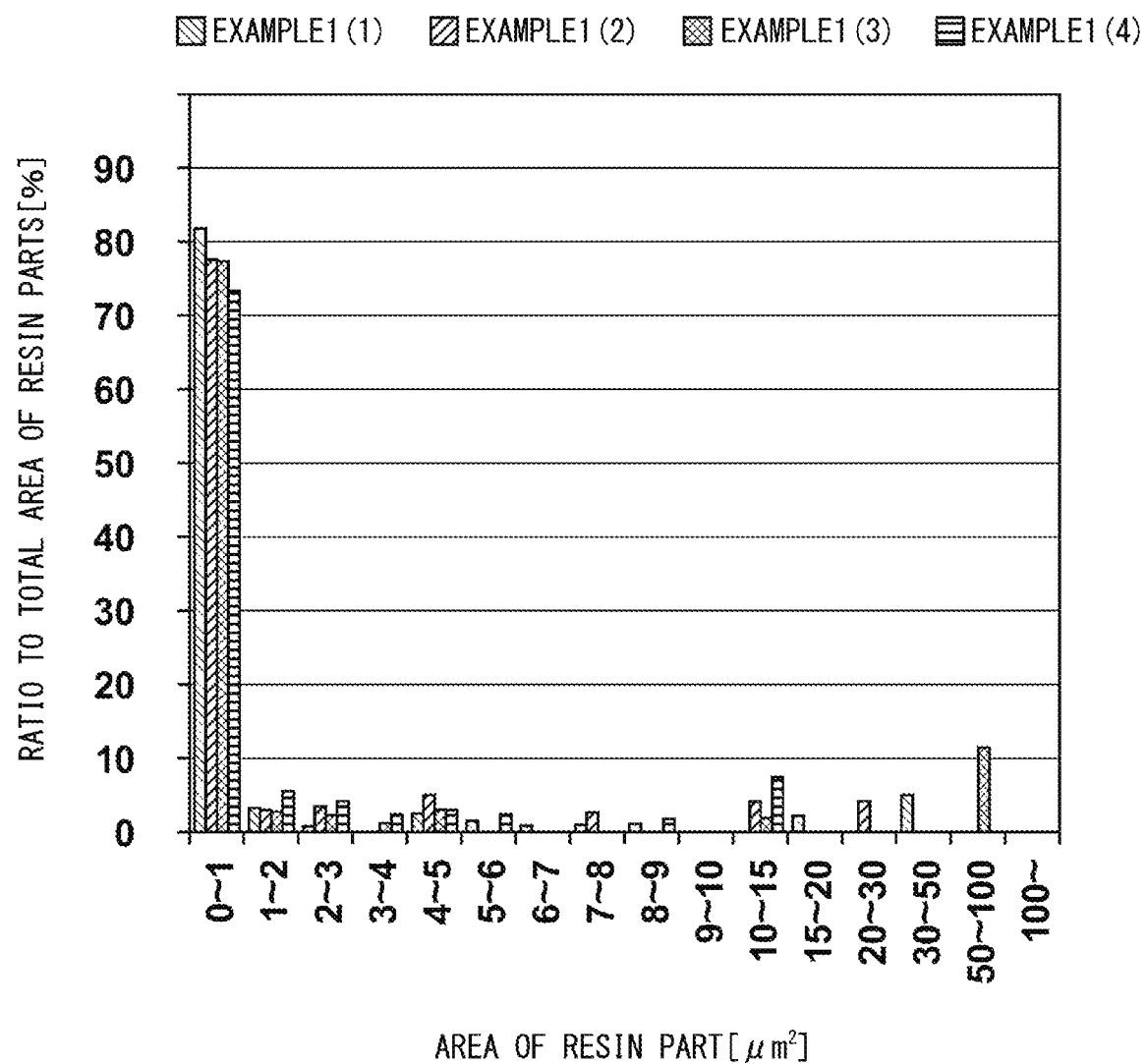
FIG. 2 is a histogram illustrating the ratio (%) of the total of areas of resin parts having a predetermined area to the total area of resin parts, on an SEM image of a membrane cross-section in the membrane thickness direction perpendicular to an inner surface of the porous membrane used in Example 1, in each region (numbers (1) to (4)) of a total of 4 visual fields with a visual field including the inner surface, a visual field including an outer surface of the membrane, and two visual fields photographed at regular intervals between those visual fields.
Figure 3:
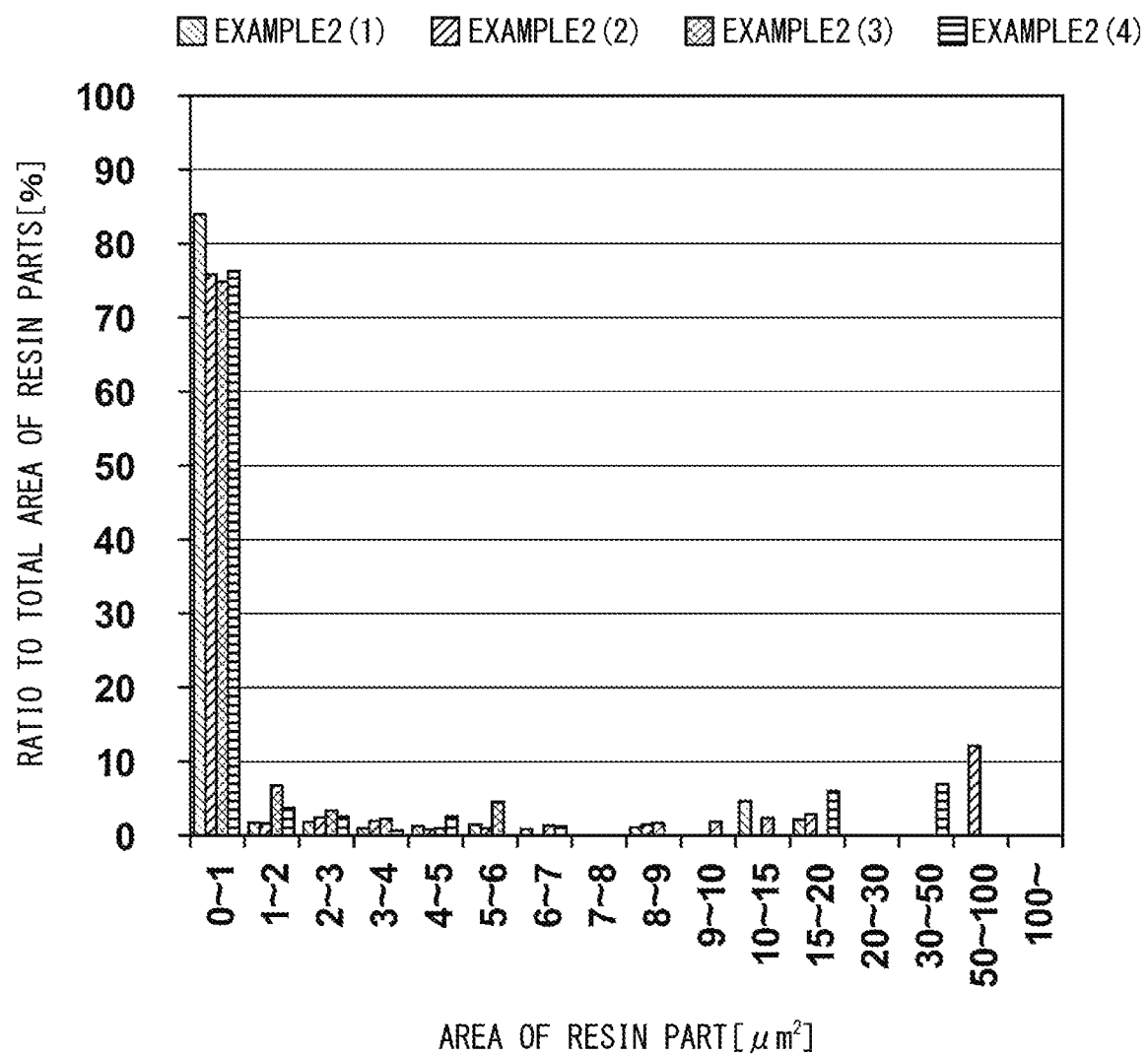
FIG. 3 is a histogram illustrating the ratio (%) of the total of areas of resin parts having a predetermined area to the total area of resin parts, on an SEM image of a membrane cross-section in the membrane thickness direction perpendicular to an inner surface of the porous membrane used in Example 2, in each region (numbers (1) to (4)) of a total of 4 visual fields with a visual field including the inner surface, a visual field including an outer surface of the membrane, and two visual fields photographed at regular intervals between those visual fields.
Figure 4:
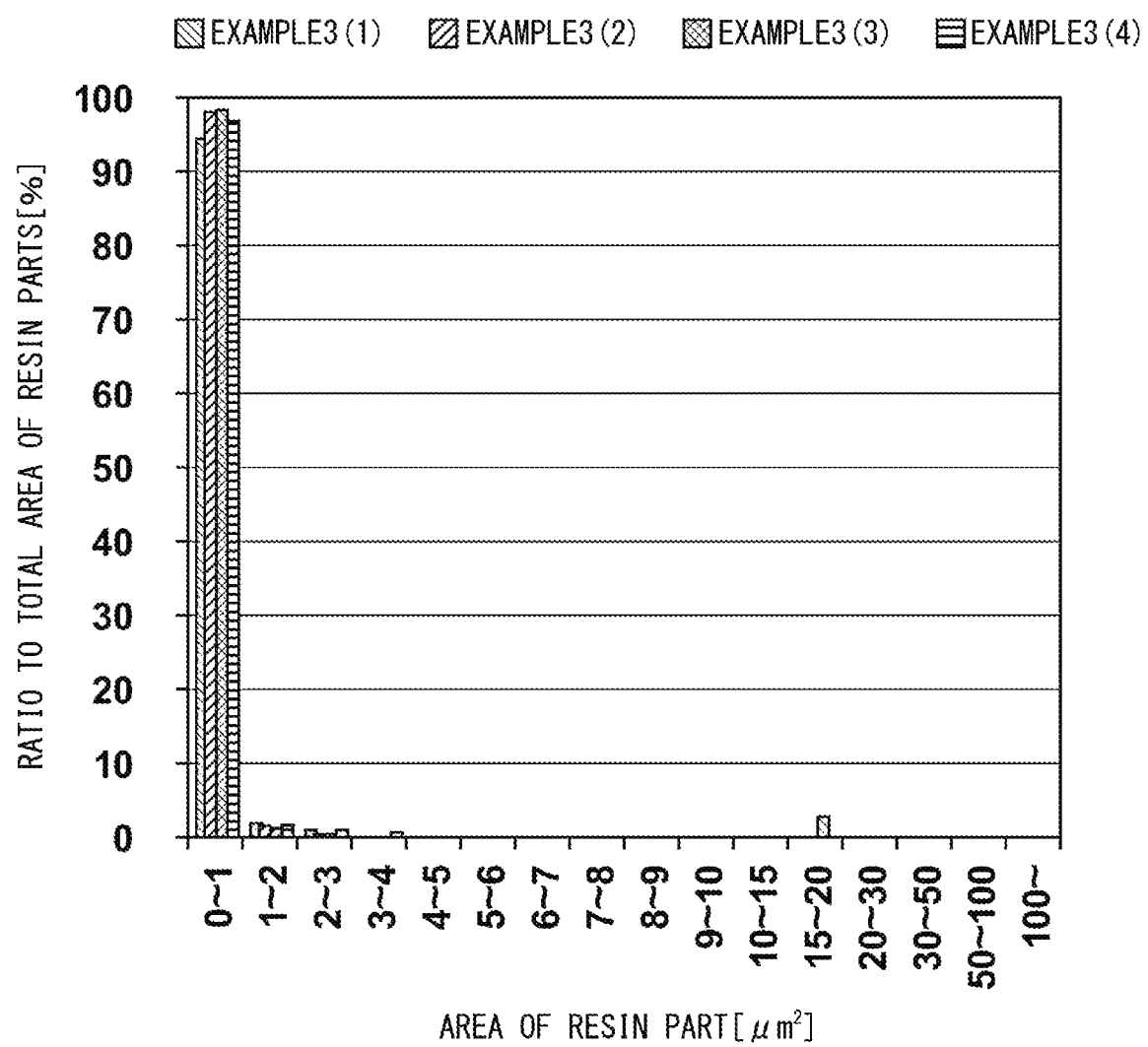
FIG. 4 is a histogram illustrating the ratio (%) of the total of areas of resin parts having a predetermined area to the total area of resin parts, on an SEM image of a membrane cross-section in the membrane thickness direction perpendicular to an inner surface of the porous membrane used in Example 3, in each region (numbers (1) to (4)) of a total of 4 visual fields with a visual field including the inner surface, a visual field including an outer surface of the membrane, and two visual fields photographed at regular intervals between those visual fields.
Figure 5:
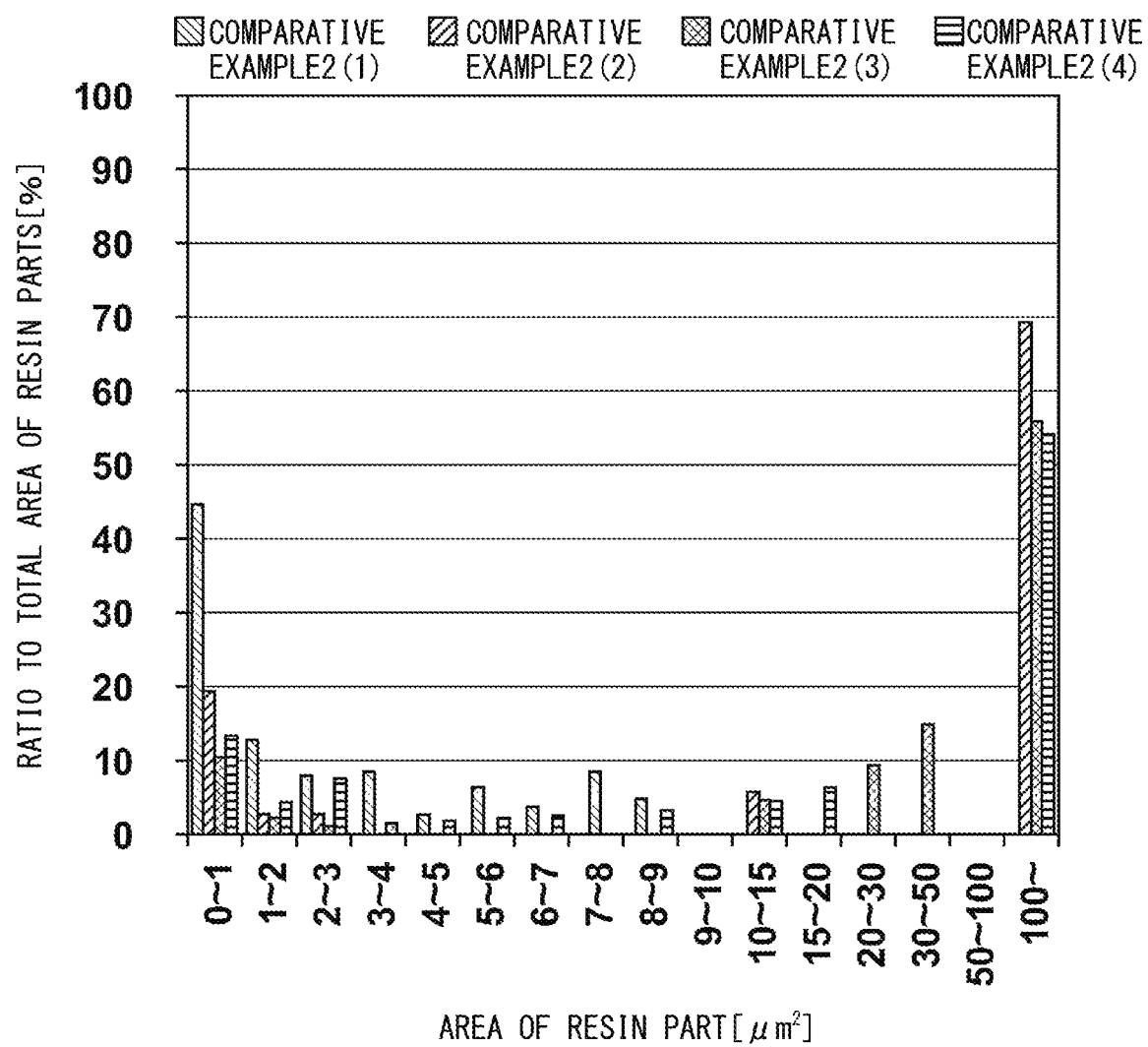
FIG. 5 is a histogram illustrating the ratio (%) of the total of areas of resin parts having a predetermined area to the total area of resin parts, on an SEM image of a membrane cross-section in the membrane thickness direction perpendicular to an inner surface of the porous membrane used in Comparative Example 2, in each region (numbers (1) to (4)) of a total of 4 visual fields with a visual field including the inner surface, a visual field including an outer surface of the membrane, and two visual fields photographed at regular intervals between those visual fields.

The embodiment of the present invention (hereinafter, sometimes referred to as the present embodiment) is described in detail below. Incidentally, the present invention is not limited to the present embodiment.

<Filtration Method>

The production method of a saccharified solution of the present embodiment includes:

a liquefaction step of adding an enzyme to liquid starch to partially degrade the starch and obtain a sugar-containing liquefied product;

a saccharification step of adding a saccharifying enzyme to the obtained sugar-containing liquefied product to further degrade the sugar and obtain a saccharified solution composition containing a saccharified solution and an insoluble component;

a filtration step of passing the saccharified solution composition through a porous membrane composed of a resin having a three-dimensional network structure to separate the saccharified solution from the insoluble component; and a cleaning step of passing or soaking the porous membrane into a cleaning solution to clean/remove an insoluble matter attached to the surface or inside of the porous membrane.

The shape of the porous membrane used in the filtration step is not particularly limited and includes a flat membrane, a tubular membrane, and a hollow-fiber membrane, but in view of space saving of the filtration apparatus, that is, for the reason that the membrane area per unit volume of the membrane module can be increased, a hollow-fiber membrane is preferred.

The filtration step in the production method of a saccharified solution of the present embodiment may be, for example, a so-called internal pressure filtration step in which a saccharified solution composition is supplied to a hollow part (inner surface) of a porous hollow-fiber membrane and allowed to pass through a thick membrane (thick wall) part of the porous hollow-fiber membrane and a liquid leached from the outer surface of the porous hollow-fiber membrane is taken out as a saccharified solution (filtrate), or may be a so-called external pressure filtration step in which a saccharified solution composition is supplied from the outer surface of the porous hollow-fiber membrane and the saccharified solution (filtrate) leached from the inner surface of the porous hollow-fiber membrane is taken out via the hollow part.

In the present description, the term "inside of the porous membrane" indicates a thick membrane (thick wall) par in which a large number of pores are formed.

In the present description, the kind and amount of the sugar contained in the "saccharified solution" are not particularly limited, but the sugar includes glucose, etc.

In addition, the kind and amount of the "insoluble component" which is contained in the saccharified solution composition and removed from the filtrate is also not particularly limited but includes, for example, protein and non-degraded starch.

In general, a purified glucose solution has been heretofore produced by liquefying a starch-containing raw material to obtain a saccharified solution composition, clarifying the composition with diatomaceous earth, furthermore subjecting it to desalting, decolorization and concentration. In the present embodiment, a predetermined porous membrane is utilized in place of the diatomaceous earth.

The cleaning step in the production method of a saccharified solution of the present embodiment includes a cleaning step of passing or soaking the porous membrane into an aqueous solution containing from 0.1 to 4 wt % of sodium hydroxide and from 0.01 to 0.5 wt % of sodium hypochlorite, serving as a cleaning solution (chemical solution), to clean the surface and inside of the porous membrane. The cleaning step may include a cleaning solution step of performing cleaning with the cleaning solution and a rinsing step of performing rinsing with rinse water for removing the remaining cleaning solution component. The cleaning step includes, for example, water backwashing of separating and removing deposits (insoluble component) from the filtration surface (saccharified solution composition supply-side surface) by passing a cleaning solution in a direction opposite the flowing direction of the saccharified solution composition in the filtration step, that is, from the saccharified solution side to the saccharified solution composition side, and air scrubbing of shaking the porous membrane with air to shake out the insoluble component attached to the porous membrane. The amount of rinse water used in the rinsing step may be preferably 100 L/m$^2$ or less, more preferably 50 L/m$^2$ or less, per unit area of the porous membrane. In addition, it is preferred that the chlorine concentration in the filtrate at the completion of the rinsing step is 0.1 ppm or less and the pH of the filtered liquid is 8.6 or less.

In the present embodiment, an aqueous solution containing from 0.1 to 4 wt % of sodium hydroxide and/or from 0.01 to 0.5 wt % of sodium hypochlorite is used as the cleaning solution (chemical solution). The concentration of sodium hydroxide in the cleaning solution (chemical solution) is more preferably from 0.5 to 4 wt %, still more preferably from 1 to 4 wt %. The concentration of sodium hypochlorite in the cleaning solution (chemical solution) is more preferably from 0.05 to 0.5 wt %, still more preferably from 0.1 to 0.5 wt %. Use of an aqueous solution containing from 0.1 to 4 wt % of sodium hydroxide and/or from 0.01 to 0.5 wt % of sodium hypochlorite makes it possible, for example, to effectively degrade/remove the insoluble component contained in the saccharified solution composition after the saccharification step.

The filtration target (to-be-treated liquid) in the filtration step of the production method of a saccharified solution of the present embodiment is a saccharified solution composition containing a saccharified solution formed in the saccharification step and an insoluble component derived from liquid starch.

The structure, raw material (material) and production method of the porous membrane used in the filtration step of the production method of a saccharified solution of the present embodiment are described in detail below.

<Porous Membrane>

The porous membrane is any of a porous membrane where on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 1 μm$^2$ or less is 70% or more relative to the total area of resin parts; a porous membrane where in each region above, the total of areas of resin parts having an area of 10 μm$^2$ or more is 15% or less relative to the total area of resin parts; and a porous membrane where in each region above, the total of areas of resin parts having an area of 1 μm$^2$ or less is 70% or more relative to the total area of resin parts and the total of areas of resin parts having an area of 10 μm$^2$ or more is 15% or less relative to the total area of resin parts. The preferable porous membrane is a membrane where in each region above, the total of areas of resin parts having an area of 1 μm$^2$ or less is 70% or more relative to the total area of resin parts, the total of areas of resin parts having an area of more than 1 μm$^2$ and less than 10 μm$^2$ is 15% or less relative to the total area of resin parts, and the total of areas of resin parts having an area of 10 μm$^2$ or more is 15% or less relative to the total area of resin parts.

FIG. 1 is one example of an SEM image of a cross-section of a porous membrane. Such an SEM image is an image resulting from binarization processing of an SEM image photograph obtained by photographing a predetermined visual field within a region closest to the inner side among, on an SEM image of a membrane cross-section in the membrane thickness direction perpendicular to an inner surface of the hollow-fiber porous membrane, the regions of a total of 4 visual fields with a visual field including the inner surface, a visual field including an outer surface of the membrane, and two visual fields photographed at regular intervals between those visual fields.

Incidentally, within each of the regions above, a difference in the existence distribution of resin parts, that is, an anisotropy of pore continuity, between the membrane cross-section in the membrane thickness direction perpendicular to the inner surface of the hollow-fiber porous membrane and the cross-section running in parallel to the inner surface can be virtually ignored.

In the present description, the term "resin part" is a dendritic skeleton portion of a three-dimensional network structure composed of a resin, which forms a large number of pores in the porous membrane. The portion indicated by black in FIG. 1 is a resin part, and the white portion is a pore.

Inside the porous membrane, a continuous pore continuing from the inner side to the outer side of the membrane while undergoing bending is formed, and when on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 1 μm$^2$ or less is 70% or more relative to the total area of resin parts, the pore continuity is high (i.e., the existence ratio of a continuous pore inside the membrane is high), leading to a high flux (amount of water permeated, water permeability) of the to-be-treated liquid and a high permeability retention after cleaning, as a result, the damage to the membrane after chemical cleaning, with the tensile elongation at break serving as an indicator thereof, is reduced. However, if the ratio of the total of areas of resin parts having an area of 1 μm$^2$ or less to the total area of resin parts is too high, the dendritic skeleton portion of a three-dimensional network structure composed of a resin, which forms a large number of pores in the porous membrane, becomes too thin. For this reason, while keeping the total of areas of resin parts having an area of 1 μm$^2$ or less to be 70% or more relative to the total area of resin parts, the resin part preferably exists such that the total of areas of resin parts having an area of more than 1 μm² is from 2 to 30% relative to the total area of resin parts, more preferably exists such that the total of areas of resin parts having an area of 10 μm² or more is 15% or less relative to the total area of resin parts, still more preferably exists such that the total of areas of resin parts having an area of more than 1 μm² and less than 10 μm² is 15% or less relative to the total area of resin parts and the total of areas of resin parts having an area of 10 μm² or more is from 2 to 15% relative to the total area of resin parts. When the resin part exists such that the total of areas of resin parts having an area of more than 1 μm² is from 2 to 30% relative to the total area of resin parts, the dendritic skeleton portion of a three-dimensional network structure composed of a resin is not too thin, so that the strength and tensile elongation at break of the porous membrane can be appropriately maintained.

FIGS. 2 to 5 are histograms illustrating the ratio (%) of the total of areas of resin parts having a predetermined area to the total area of resin parts, on an SEM image of a membrane cross-section in the membrane thickness direction perpendicular to an inner surface of the porous membranes used in Example 1, Example 2, Example 3 and Comparative Example 2, respectively, in each region (numbers (1) to 4)) of a total of 4 visual fields with a visual field including the inner surface, a visual field including an outer surface of the membrane, and two visual fields photographed at regular intervals between those visual fields. In FIG. 1, a resin part appears as particulate. In FIGS. 2 to 5, respective areas of the particulate resin parts are measured and with respect to every individual area of the particulate resin part, the ratio of the area to the total area of all resin parts in a predetermined size of visual field within each region is illustrated as a histogram Number (1) in FIGS. 2 to 5 is the number of a region closest to the inner side among, on an SEM image of a membrane cross-section in the membrane thickness direction perpendicular to an inner surface of the porous membrane, the regions of a total of 4 visual fields with a visual field including the inner surface, a visual field including an outer surface of the membrane, and two visual fields photographed at regular intervals between those visual fields, and number (4) is the number of a region closest to the inner side. For example, Example 1 number (1) is a histogram at the time of photographing a predetermined size of visual field within a region on the innermost side of the porous hollow-fiber membrane of Example 1. The method for measuring the area distribution of resin parts within each region of the porous hollow-fiber membrane is described later.

The surface opening ratio of the porous membrane is preferably from 25 to 60%, more preferably from 25 to 50%, still more preferably from 25 to 45%. When the surface opening ration on the side coming into contact with the to-be-treated liquid is 25% or more, deterioration of the water permeation performance due to clogging or abrasion of membrane surface is reduced, so that the filtration stability can be increased. On the other hand, if the surface opening ratio is high and the pore size is too large, the required separation performance may not be exerted. For this reason, the average pore size of the porous membrane is preferably from 10 to 700 nm, more preferably from 20 to 600 nm. When the average pore size is from 30 to 400 nm, the separation performance is sufficient and the pore continuity can also be ensured. The methods for measuring the surface opening ratio and the average pore size are described later.

The membrane thickness of the porous membrane is preferably from 80 to 1,000 μm, more preferably from 100 to 300 μm. When the membrane thickness is 80 μm or more, the strength of the membrane can be ensured, and on the other hand, when the membrane thickness is 1,000 μm or less, the pressure loss due to membrane resistance is reduced.

The shape of the porous hollow-fiber membrane includes an annular single-layer membrane but may be a multilayer membrane differing in the pore size between a separation layer and a support layer supporting the separation layer. In addition, the membrane may have a deformed cross-sectional structure, for example, by having a protrusion on the inner and outer surfaces of the membrane.

(Raw Material (Quality of Material) of Porous Membrane)

The resin constituting the porous membrane is preferably a thermoplastic resin, more preferably a fluororesin. The fluororesin includes a resin selected from the group consisting of a vinylidene fluoride resin (PVDF), a chlorotrifluoroethylene resin, a tetrafluoroethylene resin, an ethylene-tetrafluoroethylene copolymer (ETFE), an ethylene-monochlorotrifluoroethylene copolymer (ECTFE), a hexafluoropropylene resin, and a mixture of these resins.

The thermoplastic resin includes a polyolefin, a copolymer of olefin and halogenated olefin, a halogenated polyolefin, and a mixture thereof. The thermoplastic resin includes, for example, polyethylene, polypropylene, polyvinyl alcohol, an ethylene-vinyl alcohol copolymer, an ethylene-tetrafluoroethylene copolymer, a polyvinylidene fluoride (may contain hexafluoropropylene domains), and a mixture thereof. These resins are superior as a membrane material, because they are easy to handle due to being thermoplastic and have toughness. Among these, a vinylidene fluoride resin, a tetrafluoroethylene resin, a hexafluoropropylene resin or a mixture thereof, a homopolymer or copolymer of ethylene, tetrafluoroethylene or chlorotrifluoroethylene, and a mixture of a homopolymer and a copolymer are preferred because of excellent mechanical strength and chemical strength (resistance to chemicals) and good moldability. More specifically, the resin includes a fluororesin such as polyvinylidene fluoride, vinylidene fluoride-hexafluoropropylene copolymer, ethylene-tetrafluoroethylene copolymer and ethylene-chlorotrifluoroethylene copolymer.

The porous membrane may contain a component (e.g., impurity) other than the thermoplastic resin, in an amount of up to about 5 mass %. For example, a solvent used at the time of production of the porous membrane is contained. As described later, a first solvent (hereinafter, sometimes referred to as a nonsolvent), a second solvent (hereinafter, sometimes referred to as a good solvent or a poor solvent), which are used as a solvent at the time of production of the porous membrane, or both thereof are contained. Such a solvent can be detected by pyrolysis GC-MS (gas chromatography mass spectrometry).

The first solvent may be at least one member selected from the group consisting of sebacic acid ester, citric acid ester, acetylcitric acid ester, adipic acid ester, trimellitic acid ester, oleic acid ester, palmitic acid ester, stearic acid ester, phosphoric acid ester, a fatty acid having a carbon number of 6 to 30, and an epoxidized vegetable oil.

The second solvent is different from the first solvent and may be at least one member selected from the group consisting of sebacic acid ester, citric acid ester, acetylcitric acid ester, adipic acid ester, trimellitic acid ester, oleic acid ester, palmitic acid ester, stearic acid ester, phosphoric acid ester, a fatty acid having a carbon number of 6 to 30, and an epoxidized vegetable oil. The fatty acid having a carbon number of 6 to 30 includes capric acid, lauric acid, oleic acid, etc. The epoxidized vegetable oil includes epoxy soybean oil, epoxidized linseed oil, etc.

The first solvent is preferably a nonsolvent not allowing a thermoplastic resin to be uniformly dissolved in the first solvent even when in a first mixed solution of the thermoplastic resin and the first solvent at a ratio of 20:80, the temperature of the first mixed solution is raised to the boiling point of the first solvent.

The second solvent is preferably a good solvent allowing a thermoplastic resin to be uniformly dissolved in the second solvent when in a second mixed solution of the thermoplastic resin and the second solvent at a ratio of 20:80, the temperature of the second mixed solution is any temperature of more than 25° C. and not more than the boiling point of the second solvent.

The second solvent is more preferably a poor solvent not allowing a thermoplastic resin to be uniformly dissolved in the second solvent when in a second mixed solution of the thermoplastic resin and the second solvent at a ratio of 20:80, the temperature of the second mixed solution is 25° C., but allowing the thermoplastic resin to be uniformly dissolved in the second solvent when the temperature of the second mixed solution is any temperature of more than 100° C. and not more than the boiling point of the second solvent.

In the filtration step of the production method of a saccharified solution of the present embodiment, a porous hollow-fiber membrane using polyvinylidene fluoride (PVDF) as the thermoplastic resin and containing a first solvent (nonsolvent) may be used.

In this case, the first solvent may be a nonsolvent which is at least one member selected from the group consisting of sebacic acid ester, citric acid ester, acetylcitric acid ester, adipic acid ester, trimellitic acid ester, oleic acid ester, palmitic acid ester, stearic acid ester, phosphoric acid ester, a fatty acid having a carbon number of 6 to 30, and an epoxidized vegetable oil and which does not allow the polyvinylidene fluoride to be uniformly dissolved in the first solvent even when in a first mixed solution of polyvinylidene fluoride and the first solvent at a ratio of 20:80, the temperature of the first mixed solution is raised to the boiling point of the first solvent. The nonsolvent is preferably bis 2-ethylhexyl adipate (DOA).

The porous hollow-fiber membrane above may contain a second solvent different from the first solvent. In this case, the second solvent is preferably a good solvent which is at least one member selected from the group consisting of sebacic acid ester, citric acid ester, acetylcitric acid ester, adipic acid ester, trimellitic acid ester, oleic acid ester, palmitic acid ester, stearic acid ester, phosphoric acid ester, a fatty acid having a carbon number of 6 to 30, and an epoxidized vegetable oil and which allows the polyvinylidene fluoride to be uniformly dissolved in the second solvent when in a second mixed solution of polyvinylidene fluoride and the second solvent at a ratio of 20:80, the temperature of the second mixed solution is any temperature of more than 25° C. and not more than the boiling point of the second solvent. The second solvent is more preferably a poor solvent not allowing the polyvinylidene fluoride to be uniformly dissolved in the second solvent when the temperature of the second mixed solution is 25° C., but allowing the polyvinylidene fluoride to be uniformly dissolved in the second mixed solution is any temperature of more than 100° C. and not more than the boiling point of the second solvent. The poor solvent is preferably tributyl acetylcitrate (ATBC).

(Physical Properties of Porous Membrane)

The porous membrane is preferably a porous membrane in which the relationship between the tensile elongation at break E0 of the porous membrane before the cleaning step and the tensile elongation at break E1 of the porous membrane after the cleaning step is $E1/E0 \times 100 \geq 80\%$, and in addition, is preferably a porous membrane in which the relationship between the tensile elongation at break E0 of the porous membrane before the cleaning step and the tensile elongation at break EX of the porous membrane after repeating the cleaning step X times (X is an integer of 2 to 10) is $EX/E0 \times 100 \geq 70\%$.

The initial value of the tensile elongation at break is preferably 60% or more, more preferably 80% or more, still more preferably 100% or more, yet still more preferably 120% or more. The method for measuring the tensile elongation at break is described later.

The retention of tensile elongation at break after circulation of the chemical solution (elongation retention after cleaning by circulating the chemical solution) can serve as the indicator of the resistance to an aqueous solution containing 4 wt % of sodium hydroxide and 0.5 wt % of sodium hypochlorite (hereinafter, sometimes simply referred to as a chemical solution) (difficult of occurrence of damage to the membrane), and specifically, the tensile elongation at break after performing a series of steps by actual liquid filtration and subsequent chemical solution circulation and cleaning (corresponding to the tensile elongation at break E1 of the porous hollow-fiber membrane after the cleaning step) preferably retains 98% or more of the initial value (corresponding to the tensile elongation at break E0 before the cleaning step).

In addition, the relationship between the initial value E0 and the tensile elongation at break EX of the membrane after repeating a series of steps by actual liquid filtration and subsequent cleaning solution circulation and cleaning X times (X is an integer of 2 to 10) is preferably $EX/E0 \geq 97\%$.

In view of practical use, the compressive strength of the porous membrane is preferably 0.2 MPa or more, more preferably from 0.3 to 1.0 MPa, still more preferably from 0.4 to 1.0 MPa.

(Water Permeation Performance of Porous Membrane)

The porous membrane is preferably a porous membrane in which the relationship between the flux L0 of the porous membrane before the filtration step and the flux L1 of the porous membrane after the cleaning step is $L1/L0 \times 100 \geq 90\%$.

In addition, the porous membrane is preferably a porous membrane in which the relationship between the flux L0 of the porous membrane before the filtration step and the flux LX of the porous membrane after repeating the cleaning step X times (X is an integer of 2 to 10) is $LX/L0 \times 100 \geq 90\%$.

<Production Method of Porous Membrane>

The production method of the porous hollow-fiber membrane is described below. However, the production method of the porous hollow-fiber membrane used in the filtration method of the present embodiment is not limited to the following production method.

The production method of the porous hollow-fiber membrane used in the filtration method of the present embodiment may be a method including (a) a step of preparing a melt-kneaded product, (b) a step of feeding the melt-kneaded product to a spinning nozzle having a multiple structure, and extruding the melt-kneaded product through the spinning nozzle, thereby obtaining a hollow-fiber membrane, and (c) a step of extracting the plasticizer from the hollow-fiber membrane. In the case where the melt-kneaded product contains an additive, the method may further include, after the step (c). (d) a step of extracting the additive from the hollow-fiber membrane.

The concentration of the thermoplastic resin in the melt-kneaded product is preferably from 20 to 60 mass %, more preferably from 25 to 45 mass %, still more preferably from 30 to 45 mass %. When this value is 20 mass % or more, mechanical strength can be increased and, on the other hand, when this value is 60 mass % or less, the water permeation performance can be increased. The melt-kneaded product may contain an additive.

The melt-kneaded product may be composed of two components of a thermoplastic resin and a solvent, or may be composed of three components of a thermoplastic resin, an additive, and a solvent. The solvent contains at least a nonsolvent as described later.

As the extractant used in the step (c), a liquid being incapable of dissolving the thermoplastic resin but having high affinity for the plasticizer, such as methylene chloride or various alcohols, is preferably used.

In the case of using a melt-kneaded product containing no additive, a hollow-fiber membrane obtained through the step (c) may be used as the porous hollow-fiber membrane. In the case of producing the porous hollow-fiber membrane by using a melt-kneaded product containing an additive, it is preferable to further pass through, after the step (c). (d) a step of extracting and removing the additive from the hollow-fiber membrane to obtain a porous hollow-fiber membrane. For the extractant in the step (d), a liquid capable of dissolving the melt or additive used, such as acid or alkali, but incapable of dissolving the thermoplastic resin is preferably used.

An inorganic matter may be used as the additive. The inorganic matter is preferably an inorganic fine powder. The primary particle diameter of the inorganic fine powder contained in the melt-kneaded product is preferably 50 nm or less, more preferably 5 nm or more and less than 30 nm. Specific examples of the inorganic fine powder include silica (including finely divided silica), titanium oxide, lithium chloride, calcium chloride, and organic clay, and among these, finely divided silica is preferred in view of cost. The "primary particle diameter of the inorganic fine powder" above means a value determined from the analysis of an electron photomicrograph. More specifically, first, a group of the inorganic fine powder is pretreated by the method of ASTM D3849. Thereafter, the diameters of 3,000 to 5,000 particles in a photograph taken with a transmission electron microscope are measured, and these values are arithmetically averaged to calculate the primary particle diameter of the inorganic fine powder.

With respect to the inorganic fine powder inside the porous hollow-fiber membrane, the existing elements are identified by fluorescent X-ray, etc., and the raw material (material) of the existing inorganic fine powder can thereby be identified.

In the case of using an inorganic matter as the additive, when a hydrophilic polymer such as polyvinylpyrrolidone and polyethylene glycol is used, hydrophilicity can be imparted to the hollow-fiber membrane. In addition, when an additive with high viscosity, such as glycerin and ethylene glycol, is used, the viscosity of the melt-kneaded product can be controlled.

Next, (a) the step of preparing a melt-kneaded product in the production method of the porous hollow-fiber membrane of the present embodiment is described in detail.

In the production method of the porous hollow-fiber membrane of the present embodiment, a nonsolvent for the thermoplastic resin is mixed with a good solvent or a poor solvent. The mixed solvent after mixing is a nonsolvent for the thermoplastic resin used. When a nonsolvent is thus used as a raw material of the membrane, a porous hollow-fiber membrane having a three-dimensional network structure is obtained. The action mechanism thereof is not necessarily clear, but it is considered that when a solvent more reduced in solubility by mixing a nonsolvent is used, the crystallization of the polymer is appropriately inhibited and a three-dimensional network structure is likely to be formed. For example, the nonsolvent and the poor solvent or good solvent are selected from the group consisting of various esters, etc., such as phthalic acid ester, sebacic acid ester, citric acid ester, acetylcitric acid ester, adipic acid ester, trimellitic acid ester, oleic acid ester, palmitic acid ester, stearic acid ester, phosphoric acid ester, a fatty acid having a carbon number of 6 to 30, and an epoxidized vegetable oil.

A solvent capable of dissolving the thermoplastic resin at normal temperature is referred to as a good solvent, a solvent incapable of dissolving the thermoplastic resin at normal temperature but capable of dissolving it at high temperatures is referred to as a poor solvent for the thermoplastic resin, a solvent incapable of dissolving the thermoplastic resin even at high temperatures is referred as a nonsolvent, and whether the solvent is a good solvent, a poor solvent or a nonsolvent can be judged as follows.

About 2 g of a thermoplastic resin and about 8 g of a solvent are put in a test tube and warmed by a block heater for test tube up to the boiling point of the solvent in steps of about 10° C. and after the contents in the test tube are mixed by means of a spatula, the solvent is judged as a good solvent or a poor solvent when the thermoplastic solvent is dissolved, and judged as a nonsolvent when the thermoplastic solvent is not dissolved. The solvent is judged as a good solvent when the thermoplastic resin is dissolved at a relatively low temperature of 100° C. or less, and judged as a poor solvent when unless the temperature is raised to a high temperature of 100° C. or more and not more than the boiling point, the thermoplastic resin is not dissolved.

For example, when polyvinylidene fluoride (PVDF) is used as the thermoplastic resin and tributyl acetylcitrate (ATBC), dibutyl sebacate or dibutyl adipate is used as the solvent, PVDF uniformly mixes with the solvent at about 200° C. and dissolves. On the other hand, when bis 2-ethylhexyl adipate (DOA), diisononyl adipate or bis 2-ethylhexyl sebacate is used as the solvent, even if the temperature is raised to 250° C., PVDF is not dissolved in the solvent.

In addition, when an ethylene-tetrafluoroethyl copolymer (ETFE) is used as the thermoplastic resin and diethyl adipate is used as the solvent, ETFE uniformly mixes and dissolves at about 200° C. On the other hand, when bis 2-ethylhexyl adipate (DIBA) is used as the solvent, the resin is not dissolved.

Furthermore, when an ethylene-monochlorotrifluoroethylene copolymer (ECTFE) is used as the thermoplastic resin and triethyl citrate is used as the solvent, the resin uniformly dissolves at about 200° C., and when triphenyl phosphite (TPP) is used, the resin is not dissolved.

EXAMPLES

The present invention is described specifically below by referring to Examples, but the present invention is not limited thereto.

A saccharified solution composition as an actual liquid was produced as follows.

1. Liquefaction Stage $CaCl_2$ was added to a 31.5% aqueous slurry of cornstarch to generate 150 ppm of calcium ion and after adjusting the pH to 6.5, 1,600 units of activity of α-amylase were added thereto. The slurry was heated at 85° C. for 30 minutes, the temperature was then raised to 135° C., and the slurry was kept at the same temperature for 5 minutes. Subsequently, the temperature was again lowered to 85° C., additional 1,600 units of α-amylase were added, and the product was kept at the same temperature for 60 minutes.

2. Saccharification Stage

The liquefied starch slurry liquid was kept at a temperature of 57° C., and 0.5% β-amylase and 80 Au of glucoamylase were added thereto. Subsequently, the pH was adjusted to 4.2, and additional 80 Au of glucoamylase was added. Furthermore, saccharification for an additional 20 hours was performed.

Each of physical property values in Examples and Comparative Examples was determined by the following method.

(1) Outside Diameter and Inside Diameter of Porous Hollow-Fiber Membrane

The porous hollow-fiber membrane was thinly sliced at a cross-section perpendicular to the length direction by mans of a razor, and the outside diameter and inside diameter were measured using a 100-fold magnifying glass. With respect to one sample, the measurement was performed on 60 cut planes at intervals of 30 mm in the length direction, and average values were defined as the outside diameter and inside diameter of the hollow-fiber membrane.

(2) Electron Photomicroscopy

The porous hollow-fiber membrane was annularly cut at a cross-section perpendicular to the length direction, and 10% phosphotungstic acid+osmium tetroxide staining was conducted, followed by embedding in an epoxy resin. Subsequently, after trimming, BIB processing was applied to the sample cross-section to provide a smooth cross-section, and the cross-section was subjected to a conductive treatment to prepare a sample for microscopic examination. With respect to the prepared sample for microscopic examination, using an electron microscope, SU8000 series, manufactured by HITACHI, Ltd., an electron microscope (SEM) image of a membrane cross-section was taken at a magnification of 5,000 to 30.000 times at an accelerating voltage of 1 kV within a predetermined visual field among respective regions (circles numbers 1 to 4 in FIGS. 2 to 5) of a total of 4 visual fields with a visual field including an inner surface of the thick membrane (thick wall part) cross-section, a visual field including an outer surface of the membrane and two visual fields photographed at regular intervals between those visual fields. The measurement can be performed by changing the magnification according to the average pore size, and specifically, the magnification was set to 5,000 times when the average pore size was 0.1 μm or more, set to 10,000 times when the average pore size was 0.05 μm or more and less than 0.1 μm, and set to 30,000 times when the average pore size was less than 0.05 μm. Incidentally, the size of the visual field was set to 2,560×1,920 pixels. In the image processing, ImageJ was used, and Threshold processing (Image-Adjust-Threshold: Otsu method is selected) was applied to the photographed SEM image to binarize the image by the pore portion and the resin part.

Surface opening ratio: The surface opening ratio was measured by calculating the ratio between resin part and pore part of the binarized image.

Area distribution of resin parts: Using "Analyze Particle" command (Analyze Particle: Size 0.10-Infinity) of ImageJ, the size of each of the binarized particulate resin parts included in the photographed SEM image was measured. Denoting $\Sigma S$ as the total area of all resin parts included in the SEM image and $\Sigma S(<1~\mu m^2)$ as the area of resin parts of 1 $\mu m^2$ or less, $\Sigma S(<1~\mu m^2)/S$ was calculated, and the areal proportion of resin parts having an area of 1 $\mu m^2$ or less was thereby calculated. The areal proportion of resin parts having an area in a predetermined range was calculated in the same manner.

Incidentally, as to the noise removal at the time of applying binarization processing, resin parts having an area of less than 0.1 $\mu m^2$ were removed as a noise, and resin parts having an area of 0.1 $\mu m^2$ or more were used as the analysis target. In addition, the noise removal was performed by applying median filter processing (Process-Filters-Median; Radius: 3.0 pixels).

Particulate resin parts discontinued at an edge of the SEM image were also used as the measurement target. Furthermore, processing of "Incude Holes" (filling holes) was not performed. In addition, a processing of correcting the shape, for example, from "snowman" form to "flat" form, etc. was not performed.

Average pore size: The average pore size was measured using "Plugins-Bone J-Thickness" command of ImageJ. Incidentally, the space size is defined as a maximum circle size over which the circle cannot fit in the void.

(3) Flux (Water Permeability, Initial Pure Water Flux)

The porous hollow-fiber membrane was immersed in ethanol and then repeatedly immersed in pure water several times and thereafter, an injection needle was inserted at both ends of the wet hollow-fiber membrane having a length of about 10 cm. Pure water at 25° C. was circulated and filtered under a pressure of forming a transmembrane pressure difference of 0.03 MPa, and the amount of pure water permeated from the inner surface of the membrane was measured. The water permeability was evaluated by determining a pure water flux according to the following formula:

Initial pure water flux $[L/m^2/h]$=60×(amount of permeate [L])/{π×(inside diameter of membrane [m])×(effective length of membrane [m])×(measurement time [min])}

Here, the "effective length of membrane" indicates a net membrane length excluding a portion into which the injection needle is inserted.

(4) Actual Liquid Filtration Method

The saccharified solution composition to be filtered as an actual liquid had specifically Brix=32.5% and turbidity of 360 NTU.

First, (i) pure water was charged into a circulation vessel and by performing circulation/filtration to create a transmembrane pressure difference of 0.03 MPa, the permeate was collected for 2 minutes and defined as the initial water permeability.

Next, (ii) after draining off water from the piping, 100 mL of the saccharified solution composition was charged into the circulation vessel and circulated/filtered to create a transmembrane pressure difference of 0.1 MPa until it was 90% recovered as a saccharified solution on the filtered side.

Subsequently, (iii) after draining off the saccharified solution composition from the piping, pure water was charged into the circulation vessel and circulated/filtered to create a transmembrane pressure difference of 0.03 MPa, thereby performing water washing.

Furthermore, (iv) after draining off water from the piping, a prepared chemical solution was charged into the circulation vessel and caused to undergo membrane circulation/filtration, thereby performing chemical cleaning for 30 minutes. For the chemical solution, an aqueous solution having mixed therein 0.5% of sodium hypochlorite and 4% caustic soda was used.

Then, after draining off the chemical solution from the piping, pure water was charged into the circulation vessel and circulated/filtered to create a transmembrane pressure difference of 0.03 MPa, the permeate drawn was repeatedly collected at a timing of 10 L/m², the water washing was terminated when the chlorine concentration and pH of the permeate became 0.1 ppm or less and 8.6 or less, respectively, and the amount of the rinse water was recorded. Successively, circulation/filtration was performed with the same transmembrane pressure difference, and the permeate was collected for 2 minutes, taken as the water permeability and compared with the initial water permeability.

Incidentally, each parameter was calculated according to the following formula:

transmembrane pressure difference={(input pressure)+(output pressure)}/2 membrane inner surface area [m²]=π×(inside diameter of hollow-fiber membrane [m])×(effective length of hollow-fiber membrane [m])

membrane surface linear velocity [m/s]=4×(amount of circulating water [m³/s])/{×(inside diameter of membrane [m])²}

All operations were performed at 25° C. and a membrane surface linear velocity of 1.0 m/sec.

(5) Tensile Elongation at Break (%)

The porous hollow-fiber membrane was directly used as the sample, and the tensile elongation at break was calculated in conformity with JIS K7161. The load and displacement at the time of tensile fracture were measured under the following conditions.

Measurement device: Instron tensile tester (AGS-5D, manufactured by Shimadzu Corporation)

Chuck-to-chuck distance: 5 cm

Tensile speed: 20 cm/min (6) 0.5 wt % Sodium Hypochlorite and 4% Sodium Hydroxide (Chemical Solution) Resistance Test A series of steps by actual liquid filtration and subsequent chemical solution circulation and cleaning, described in (4) above, was repeated 10 times. Denoting E0 as the initial value of the tensile elongation at break (tensile elongation at break before immersion) and E10 as the value of tensile elongation at break of the porous hollow-fiber membrane after repeating the cleaning step 10 times, E10/E0 was calculated as the "retention (%) of the tensile elongation at break after repeating 10 chemical cleaning cycles", and the chemical resistance was evaluated.

In addition, denoting L0 (flux L0) as the initial pure water permeability and L10 (flux L10) as the water permeability after the cleaning step of repeating 10 times a series of steps (4) by actual liquid filtration and subsequent cleaning solution circulation and cleaning, L10/L0 was calculated as the "water permeability retention (%) after repeating 10 chemical cleaning cycles".

Example 1

A melt-kneaded product was prepared using 40 mass % of PVDF resin (KF-W #1000, produced by Kureha Corporation) as a thermoplastic resin, 23 mass % of finely divided silica (primary particle diameter: 16 nm), 32.9 mass % of bis 2-ethylhexyl adipate (DOA) as a nonsolvent, and 4.1 mass % of tributyl acetylcitrate (ATBC, boiling point: 343° C.) as a poor solvent. The temperature of the obtained melt-kneaded product was 240° C. The obtained melt-kneaded product was extruded using a spinning nozzle having a double tube structure to pass a hollow-fiber extrudate through a free running distance of 120 mm and then solidified in water at 30° C., and a porous structure was developed by a thermally induced phase separation method. The obtained hollow-fiber extrudate was taken out at a rate of 5 m/min and wound on a reel. The wound hollow-fiber extrudate was immersed in isopropyl alcohol to extract and remove DOA and ATBC, then immersed in water for 30 minutes to water-displace the hollow-fiber membrane, and subsequently immersed in an aqueous 20 mass % NaOH solution at 70° C. for 1 hour. Furthermore, water washing was repeated, and finely divided silica was thereby extracted and removed to produce a porous hollow-fiber membrane.

The formulation, production conditions and various physical properties of the obtained porous membrane are shown in Table 1 below. The obtained porous hollow-fiber membrane had a three-dimensional network structure and was a membrane with high pore continuity, in which the flux (water permeability) was high and the flux (time until 90% recovery) in the first to tenth batch of actual liquid was from 61 to 65 minutes. In addition, the retention of the tensile elongation at break after immersion in chemical solution was 98%, and the retention of the tensile elongation at break after repeating 10 chemical cleaning cycles was also as high as 98%. Furthermore, the retention of the water permeability after immersion in chemical solution was 92%, and the retention of the water permeability after repeating 10 chemical cleaning cycles was 93%. Thus, the water permeability could be maintained, and an increase in the pore size of the membrane due to deterioration by the chemical solution was not observed.

Example 2

A melt-kneaded product was prepared using 40 mass % of ETFE resin (TL-081, produced by AGC Inc.) as a thermoplastic resin, 23 mass % of finely divided silica (primary particle diameter: 16 nm), 32.9 mass % of bis 2-ethylhexyl adipate (DOA) as a nonsolvent, and 4.1 mass % of diisobutyl adipate (DIBA) as a poor solvent. The temperature of the obtained melt-kneaded product was 240° C. The obtained melt-kneaded product was extruded using a spinning nozzle having a double tube structure to pass a hollow-fiber extrudate through a free running distance of 120 mm and then solidified in water at 30° C., and a porous structure was developed by a thermally induced phase separation method. The obtained hollow-fiber extrudate was taken out at a rate of 5 m/min and wound on a reel. The wound hollow-fiber extrudate was immersed in isopropyl alcohol to extract and remove DOA and DIBA, then immersed in water for 30 minutes to water-displace the hollow-fiber membrane, and subsequently immersed in an aqueous 20 mass % NaOH solution at 70° C. for 1 hour. Furthermore, water washing was repeated, and finely divided silica was thereby extracted and removed to produce a porous hollow-fiber membrane.

The formulation, production conditions and various physical properties of the obtained porous membrane are shown in Table 1 below. The obtained porous hollow-fiber membrane had a three-dimensional network structure and was a membrane with high pore continuity, in which the flux (water permeability) was high and the flux (time until 90% recovery) in the first to tenth batch of actual liquid was from 60 to 65 minutes. In addition, the retention of the tensile elongation at break after immersion in chemical solution was 99%, and the retention of the tensile elongation at break after repeating 10 chemical cleaning cycles was as high as 97%. Furthermore, the retention of the water permeability after immersion in chemical solution was 90%, and the retention of the water permeability after repeating 10 chemical cleaning cycles was 92%. Thus, the water permeability could be maintained, and an increase in the pore size of the membrane due to deterioration by the chemical solution was not observed.

Example 3

A melt-kneaded product was prepared using 40 mass % of ECTFE resin (Halar901, produced by Solvay Specialty Polymers Ltd.) as a thermoplastic resin, 23 mass % of finely divided silica (primary particle diameter: 16 nm), 32.9 mass % of triphenyl phosphite (TPP) as a nonsolvent, and 4.1 mass % of bis 2-ethylhexyl adipate (DOA) as a poor solvent. The temperature of the obtained melt-kneaded product was 240° C. The obtained melt-kneaded product was extruded using a spinning nozzle having a double tube structure to pass a hollow-fiber extrudate through a free running distance of 120 mm and then solidified in water at 30° C., and a porous structure was developed by a thermally induced phase separation method. The obtained hollow-fiber extrudate was taken out at a rate of 5 m/min and wound on a reel. The wound hollow-fiber extrudate was immersed in isopropyl alcohol to extract and remove TPP and DOA, then immersed in water for 30 minutes to water-displace the hollow-fiber membrane, and subsequently immersed in an aqueous 20 mass % NaOH solution at 70° C. for 1 hour. Furthermore, water washing was repeated, and finely divided silica was thereby extracted and removed to produce a porous hollow-fiber membrane.

The formulation, production conditions and various physical properties of the obtained porous membrane are shown in Table 1 below. The obtained porous hollow-fiber membrane had a three-dimensional network structure and was a membrane with high pore continuity, in which the flux (water permeability) was high and the flux (time until 90% recovery) in the first to tenth batch of actual liquid was from 59 to 67 minutes. In addition, the retention of the tensile elongation at break after immersion in chemical solution was 98%, and the retention of the tensile elongation at break after repeating 10 chemical cleaning cycles was as high as 97%. Furthermore, the retention of the water permeability after immersion in chemical solution was 93%, the retention of the water permeability after repeating 10 chemical cleaning cycles was 90%, and deterioration by the chemical solution was not observed.

Comparative Example 1

The hollow-fiber membrane of Comparative Example 1 was obtained by performing membrane formation in the same manner as in Example 1 except that the solvent was only ATBC. The formulation, production conditions and various physical properties of the obtained porous membrane are shown in Table 1 below. The obtained porous hollow-fiber membrane had a spherulite structure and was a membrane with low pore continuity, in which the flux was low and the flux (time until 90% recovery) in the first to tenth batch of actual liquid was from 1.067 to 1,254 minutes. The retention of the tensile elongation at break after immersion in chemical solution was as low as 85%.

Comparative Example 2

The hollow-fiber membrane of Comparative Example 2 was obtained by performing membrane formation in the same manner as in Example 1 except that the content of finely divided silica was 0% and the solvent was only γ-butyrolactone. The formulation, production conditions and various physical properties of the obtained porous membrane are shown in Table 1 below. The obtained porous hollow-fiber membrane had a spherulite structure and was a membrane with low pore continuity, in which the flux was low and the flux (time until 90% recovery) in the first to tenth batch of actual liquid was from 125 to 138 minutes. The retention of the tensile elongation at break after immersion in chemical solution was as low as 86%.

Comparative Example 3

The hollow-fiber membrane of Comparative Example 3 was obtained by performing membrane formation in the same manner as in Example 3 except that the solvent was only DOA. The formulation, production conditions and various physical properties of the obtained porous membrane are shown in Table 1 below. The obtained porous hollow-fiber membrane had a spherulite structure and was a membrane with low pore continuity, in which the flux was low and the flux (time until 90% recovery) in the first to tenth batch of actual liquid was from 1,125 to 1,246 minutes. The retention of the tensile elongation at break after immersion in chemical solution was as low as 84%.

TABLE 1

|  | Example | | | Comparative Example 1 | Comparative Example 2 | Comparative Example 3 |
| --- | --- | --- | --- | --- | --- | --- |
|  | Example 1 | Example 2 | Example 3 |  |  |  |
| Resin | PVDF KF W#1000 40% | ETFE TL-081 40% | ECTFE Halar901 40% | PVDF KF W#1000 40% | PVDF KF W#1000 40% | ECTFE Halar901 40% |
| Additive | finely divided silica 23% | finely divided silica 23% | finely divided silica 23% | finely divided silica 23% | none | finely divided silica 23% |
| Nonsolvent | DOA: 32.9% | DOA: 32.9% | TPP: 32.9% | none | none | none |
| Poor solvent | ATBC: 4.1% | DIBA: 4.1% | DOA: 4.1% | ATBC: 37% | γ-butyrolactone: 60% | DOA: 4.1% |
| Discharge temperature of membrane-forming stock solution [° C.] | 240 | 240 | 240 | 240 | 200 | 240 |
| Coagulating liquid | water | water | water | water | water | water |
| Coagulating liquid temperature [° C.] | 30 | 30 | 30 | 30 | 30 | 30 |
| Free running distance [mm] | 120 | 120 | 120 | 120 | 120 | 120 |
| Average pore size [nm] | 500 | 600 | 400 | 200 | 100 | 100 |

TABLE 1-continued

| | Example 1 | Example 2 | Example 3 | Comparative Example 1 | Comparative Example 2 | Comparative Example 3 |
|---|---|---|---|---|---|---|
| Pore structure | three-dimensional network | three-dimensional network | three-dimensional network | spherulite | spherulite | spherulite |
| Surface opening ratio [%] | 30 | 30 | 30 | 20 | 20 | 20 |
| Flux (water permeability) [L/($m^2 \cdot h$)] | 4,000 | 5,000 | 3,500 | 150 | 2,000 | 100 |
| Outside diameter/inside diameter [mm] | 1.2/0.7 | 1.2/0.7 | 1.2/0.7 | 1.2/0.7 | 1.2/0.7 | 1.2/0.7 |
| Tensile elongation at break [%] | 170 | 160 | 180 | 30 | 40 | 30 |
| Retention of tensile elongation at break after immersion in chemical solution E1/E0 [%] | 98 | 99 | 98 | 85 | 86 | 84 |
| Retention of water permeability after immersion in chemical solution L1/L0 [%] | 92 | 90 | 93 | 53 | 56 | 52 |
| Retention of tensile elongation at break after repeating 10 chemical cleaning cycles E10/E0 [%] | 98 | 97 | 97 | 61 | 64 | 62 |
| Retention of water permeability after repeating 10 chemical cleaning cycles L10/L0 [%] | 93 | 92 | 90 | 43 | 37 | 41 |
| Ratio of resin parts of 1 $um^2$ or less by image analysis (1) | 82 | 84 | 94 | 18 | 45 | 10 |
| Ratio of resin parts of 1 $um^2$ or less by image analysis (2) | 78 | 76 | 98 | 17 | 19 | 19 |
| Ratio of resin parts of 1 $um^2$ or less by image analysis (3) | 77 | 75 | 98 | 15 | 10 | 10 |
| Ratio of resin parts of 1 $um^2$ or less by image analysis (4) | 73 | 76 | 97 | 14 | 13 | 13 |
| Ratio of resin parts of 10 $um^2$ or more by image analysis (1) | 7 | 7 | 3 | 63 | 0 | 87 |
| Ratio of resin parts of 10 $um^2$ or more by image analysis (2) | 8 | 15 | 0 | 68 | 75 | 75 |
| Ratio of resin parts of 10 $um^2$ or more by image analysis (3) | 13 | 2 | 0 | 55 | 85 | 85 |
| Ratio of resin parts of 10 $um^2$ or more by image analysis (4) | 7 | 13 | 0 | 75 | 65 | 65 |
| Flux (time until 90% recovery, min) in first batch of actual liquid | 62 | 65 | 59 | 1067 | 125 | 1125 |
| Flux (time until 90% recovery, min) in second batch of actual liquid | 65 | 60 | 67 | 1254 | 126 | 1283 |
| Flux (time until 90% recovery, min) in tenth batch of actual liquid | 61 | 63 | 65 | 1200 | 138 | 1246 |
| Amount of rinse water when chlorine concentration and pH of permeated liquid after chemical cleaning became 0.1 ppm or less and 8.6 or less, respectively (L/$m^2$) | 40 | 40 | 30 | 220 | 210 | 210 |

It is seen from the results above that a membrane with good pore continuity is excellent in the chemical resistance and filtration performance and has an enhanced life.

INDUSTRIAL APPLICABILITY

The filtration step in the production method of a saccharified solution according to the present invention uses a membrane having good pore continuity from the inner side of membrane, which is a to-be-treated liquid side of a porous filtration membrane, to the outer side of membrane, which is a filtrate side, so that in the case where an aqueous solution containing from 0.1 to 4 wt % of sodium hydroxide and/or from 0.01 to 0.5 wt % of sodium hypochlorite is employed as a cleaning solution (chemical solution) used in the cleaning step, the deterioration of the membrane can be kept to a minimum and excellent chemical resistance and filtration performance as well as an enhanced life can be achieved.

The invention claimed is:
1. A method for producing a saccharified solution, comprising the following steps:
   a liquefaction step of adding an enzyme to liquid starch to partially degrade the starch and obtain a sugar-containing liquefied product;
   a saccharification step of adding a saccharifying enzyme to the obtained sugar-containing liquefied product to further degrade the sugar and obtain a saccharified solution composition containing a saccharified solution and an insoluble component;
   a filtration step of passing the saccharified solution composition through a porous membrane composed of a resin having a three-dimensional network structure to separate the saccharified solution from the insoluble component; and
   a cleaning step of passing or soaking the porous membrane into a cleaning solution to clean/remove an insoluble matter attached to the surface or inside of the porous membrane; wherein on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 1 $\mu m^2$ or less is 70% or more relative to the total area of resin parts, and the cleaning solution is an aqueous solution containing from 0.1 to 4 wt % of sodium hydroxide and from 0.01 to 0.5 wt % of sodium hypochlorite.

2. A method for producing a saccharified solution, comprising the following steps:

a liquefaction step of adding an enzyme to liquid starch to partially degrade the starch and obtain a sugar-containing liquefied product;

a saccharification step of adding a saccharifying enzyme to the obtained sugar-containing liquefied product to further degrade the sugar and obtain a saccharified solution composition containing a saccharified solution and an insoluble component;

a filtration step of passing the saccharified solution composition through a porous membrane composed of a resin having a three-dimensional network structure to separate the saccharified solution from the insoluble component; and a cleaning step of passing or soaking the porous membrane into a cleaning solution to clean/remove an insoluble matter attached to the surface or inside of the porous membrane; wherein on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 10 $\mu m^2$ or more is 15% or less relative to the total area of resin parts, and the cleaning solution is an aqueous solution containing from 0.1 to 4 wt % of sodium hydroxide and from 0.01 to 0.5 wt % of sodium hypochlorite.

3. A method for producing a saccharified solution, comprising the following steps:

a liquefaction step of adding an enzyme to liquid starch to partially degrade the starch and obtain a sugar-containing liquefied product;

a saccharification step of adding a saccharifying enzyme to the obtained sugar-containing liquefied product to further degrade the sugar and obtain a saccharified solution composition containing a saccharified solution and an insoluble component;

a filtration step of passing the saccharified solution composition through a porous membrane composed of a resin having a three-dimensional network structure to separate the saccharified solution from the insoluble component; and a cleaning step of passing or soaking the porous membrane into a cleaning solution to clean/remove an insoluble matter attached to the surface or inside of the porous membrane; wherein on an SEM image of a membrane cross-section in the membrane thickness direction perpendicular to an inner surface of the porous membrane, in each region of a total of 4 visual fields with a visual field including the inner surface, a visual field including an outer surface of the membrane, and two visual fields photographed at regular intervals between those visual fields, the total of areas of resin parts having an area of 1 $\mu m^2$ or less is 70% or more relative to the total area of resin parts, and the total of areas of resin parts having an area of 10 $\mu m^2$ or more is 15% or less relative to the total area of resin parts, and the cleaning solution is an aqueous solution containing from 0.1 to 4 wt % of sodium hydroxide and from 0.01 to 0.5 wt % of sodium hypochlorite.

4. The method according to any one of claims 1 to 3, wherein the surface opening ratio of the porous membrane is from 25 to 60%.

5. The method according to any one of claims 1 to 3, wherein the relationship between the tensile elongation at break E0 of the porous membrane before the cleaning step and the tensile elongation at break E1 of the porous membrane after the cleaning step is $E1/E0 \times 100 \geq 98\%$.

6. The method according to any one of claims 1 to 3, wherein the relationship between the tensile elongation at break E0 of the porous membrane before the cleaning step and the tensile elongation at break EX of the porous membrane after repeating the cleaning step X times (X is an integer of 2 to 10) is $EX/E0 \times 100 \geq 97\%$.

7. The method according to any one of claims 1 to 3, wherein the relationship between the flux L0 of the porous membrane before the filtration step and the flux L1 of the porous membrane after the cleaning step is $L1/L0 \times 100 \geq 90\%$.

8. The method according to any one of claims 1 to 3, wherein the relationship between the flux L0 of the porous membrane before the filtration step and the flux LX of the porous membrane after repeating the cleaning step X times (X is an integer of 2 to 10) is $LX/L0 \times 100 \geq 90\%$.

9. The method according to any one of claims 1 to 3, wherein the porous membrane is a hollow-fiber membrane.

10. The method according to any one of claims 1 to 3, wherein the resin constituting the porous membrane is a thermoplastic resin.

11. The method according to claim 10, wherein the thermoplastic resin is a fluororesin.

12. The method according to claim 11, wherein the fluororesin is selected from the group consisting of a vinylidene fluoride resin (PVDF), a chlorotrifluoroethylene resin, a tetrafluoroethylene resin, an ethylene-tetrafluoroethylene copolymer (ETFE), an ethylene-monochlorotrifluoroethylene copolymer (ECTFE), a hexafluoropropylene resin, and a mixture of these resins.

13. The method according to any one of claims 1 to 3, wherein the cleaning step includes a cleaning solution step of performing cleaning with the cleaning solution and a rinsing step of performing rinsing with rinse water for removing the remaining cleaning solution component.

14. The method according to claim 13, wherein the amount of rinse water used in the rinsing step is 100 L/m² or less per unit area of the porous membrane.

15. The method according to claim 13, wherein the chlorine concentration in the filtrate at the completion of the rinsing step is 0.1 ppm or less and the pH of the filtered liquid is 8.6 or less.

* * * * *